United States Patent
Cho et al.

(10) Patent No.: US 10,317,334 B2
(45) Date of Patent: Jun. 11, 2019

(54) ACHROMATIC ROTATING-ELEMENT ELLIPSOMETER AND METHOD FOR MEASURING MUELLER-MATRIX ELEMENTS OF SAMPLE USING THE SAME

(71) Applicant: KOREA RESEARCH INSTITUTE OF STANDARDS AND SCIENCE, Daejeon (KR)

(72) Inventors: Yong Jai Cho, Daejeon (KR); Won Chegal, Daejeon (KR); Hyun Mo Cho, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 0 days.

(21) Appl. No.: 15/557,446

(22) PCT Filed: Mar. 8, 2016

(86) PCT No.: PCT/KR2016/002287
§ 371 (c)(1),
(2) Date: Sep. 11, 2017

(87) PCT Pub. No.: WO2016/148422
PCT Pub. Date: Sep. 22, 2016

(65) Prior Publication Data
US 2018/0113069 A1 Apr. 26, 2018

(30) Foreign Application Priority Data
Mar. 13, 2015 (KR) .......... 10-2015-0034847

(51) Int. Cl.
*G01J 4/04* (2006.01)
*G01N 21/21* (2006.01)
(Continued)

(52) U.S. Cl.
CPC ........ *G01N 21/211* (2013.01); *G01B 11/0641* (2013.01); *G01J 4/04* (2013.01); *G01N 21/8422* (2013.01)

(58) Field of Classification Search
CPC ........ G01J 4/00; G01J 4/02; G01J 4/04; G01J 2004/001; G01J 2004/002;
(Continued)

(56) References Cited

U.S. PATENT DOCUMENTS 8,447,546 B2 * 5/2013 Cho .......................... G01J 1/42
702/66
8,830,463 B2 * 9/2014 Cho ..................... G01N 21/211
356/369

(Continued)

FOREIGN PATENT DOCUMENTS

| KR | 1020010053381 A | 6/2001 |
| KR | 1020020008697 A | 1/2002 |
| KR | 1020100064612 A | 6/2010 |
| KR | 101270260 B1 | 5/2013 |

OTHER PUBLICATIONS

ISA European Patent Office, International Search Report Issued in Application No. PCT/EP2015/050424, dated Jun. 10, 2016, WIPO, 4 pages.

*Primary Examiner* — Gordon J Stock, Jr.
(74) *Attorney, Agent, or Firm* — McCoy Russell LLP

(57) ABSTRACT

The present invention relates to an optical element rotation type ellipsometer, and more particularly, to an ellipsometer used to measure Mueller-matrix components of a sample by measuring and analyzing a change in a polarization state of light reflected or transmitted by the sample.

According to the exemplary embodiment of the present invention, it is possible to provide the achromatic rotating-element ellipsometer and the method for measuring Mueller-matrix elements of a sample using the same capable of (Continued)

measuring the Mueller-matrix elements of the anisotropic sample as well as the isotropic sample by using four polarizers.

10 Claims, 3 Drawing Sheets

(51) Int. Cl.
*G01B 11/06* (2006.01)
*G01N 21/84* (2006.01)

(58) Field of Classification Search
CPC ........... G01J 2004/004; G01J 2004/005; G01J 2004/007; G01J 2004/008; G01N 2201/061; G01N 2201/0633; G01N 2201/0683; G01N 2201/11; G01N 21/211; G01N 2021/213; G01N 2021/214; G01N 2021/215
See application file for complete search history.

(56) References Cited

U.S. PATENT DOCUMENTS

| | | | |
|---|---|---|---|
| 9,581,498 B2* | 2/2017 | Cho | G01J 3/447 |
| 10,145,785 B2* | 12/2018 | Cho | G01N 21/211 |
| 2007/0146706 A1 | 6/2007 | Garcia-Caurel et al. | |
| 2013/0044318 A1* | 2/2013 | Cho | G01N 21/211 356/369 |
| 2016/0153894 A1* | 6/2016 | Cho | G01N 21/211 356/364 |

* cited by examiner

ACHROMATIC ROTATING-ELEMENT ELLIPSOMETER AND METHOD FOR MEASURING MUELLER-MATRIX ELEMENTS OF SAMPLE USING THE SAME

CROSS-REFERENCE TO RELATED APPLICATIONS

The present application is a U.S. National Phase of International Patent Application Serial No. PCT/KR2016/002287, entitled "CHROMATIC ABERRATION-FREE OPTICAL ELEMENT-ROTATION TYPE ELLIPSOMETER AND METHOD OF MEASURING MUELLER-MATRIX OF SPECIMEN USING SAME," filed on Mar. 8, 2016. International Patent Application Serial No. PCT/KR2016/002287 claims priority to Korean Patent Application No. 10-2015-0034847, filed on Mar. 13, 2015.

TECHNICAL FIELD

The present invention relates to an optical element rotation type ellipsometer and, more specifically, to an ellipsometer used for measuring and analyzing a change in a polarization state of light reflected by or transmitted through a sample to measure Mueller-matrix elements of the sample.

BACKGROUND ART

In a manufacturing process of industrial fields associated with a semiconductor device, a flat panel display, a nano-bio, a nano-imprint, thin film optics, and the like, that have been rapidly developed, importance of a technology capable of contactlessly measuring and evaluating a thickness of a thin film and a shape and physical properties of a nano pattern without damaging nano samples has more and more increased.

In accordance with the continuous development of these industrial fields, the thickness of the thin film has been gradually decreased to arrive at a level of several atom layers, and the shape of the nano pattern has become complicated from an existing two-dimensional structure to a three-dimensional structure. Therefore, a process measurement technique is needed to more accurately analyze the shape and physical properties of nanoscale samples.

Among the techniques for contactlessly measuring the shape and physical properties of samples, an ellipsometer and a method using the same have been widely used with development of a light source, a photodetector, and a computer.

Korean Patent No. 1270260 discloses an ellipsometer for measuring a shape and physical properties of a sample according to the related art and a measurement method using the same.

DISCLOSURE

Technical Problem

An optical element rotation type ellipsometer according to the related art additionally installs a polarizer in a stop state after a light source in an optical path of a polarizer rotating type multi-channel spectroscopic ellipsometer to make the light source into linear polarization, thereby solving a residual polarization problem of the light source and additionally installs a polarizer in a stop state before a multi-channel spectrometer in an optical path of an analyzer rotating type multi-channel spectroscopic ellipsometer to transmit linearly polarized light to the photodetector, thereby solving a polarization dependency problem of the photodetector.

However, the optical element rotation type ellipsometer according to the related art may use three polarizers to be able to find the Fourier coefficients of the optical power waveform, the ellipsometric angle of the sample, and the unpolarized reflectance of the sample from the measured exposure amount, but the related art does not specifically propose the method for measuring Mueller-matrix elements of the anisotropic sample. Therefore, to detect the shape and physical properties of the anisotropic sample, the related art has the problem in that the additional measurements such as rotating the direction of the sample or scanning the fixed optical element are required.

Technical Solution

In one general aspect, an achromatic rotating-element ellipsometer includes: a light source configured to radiate incident light toward a sample; a fixed polarizer configured to be disposed between the light source and the sample on a travel path of the incident light and polarize the incident light radiated from the light source; a constant speed rotation polarizer configured to be disposed between the fixed polarizer and the sample on the travel path of the incident light, have the light passing through the fixed polarizer be incident thereon, and rotate at a constant speed for polarizing the incident light; a constant speed rotation analyzer configured to have the light polarized by passing through the constant speed rotation polarizer incident thereon and rotate at a constant speed for polarizing the incident light, with the polarization state of the light polarized by passing through the constant speed rotation polarizer being changed by being reflected from or transmitted through the sample; a fixed analyzer configured to have the light polarized by passing through the constant speed rotation analyzer incident thereon and polarize the incident light; and a photodetector configured to have the light polarized by passing through the fixed analyzer incident thereon, detect an exposure of the incident light, and output a value of a radiant flux of light corresponding to the exposure.

The achromatic rotating-element ellipsometer may further include: a first hollow shaft stepping motor configured to be attached to the fixed polarizer to control an azimuth of the fixed polarizer; a second hollow shaft constant speed rotation motor configured to be attached to the constant speed rotation polarizer to rotate the constant speed rotation polarizer at a constant speed; a third hollow shaft constant speed rotation motor configured to be attached to the constant speed rotation analyzer to rotate the constant speed rotation analyzer at a constant speed; a fourth hollow shaft stepping motor configured to be attached to the fixed analyzer to control an azimuth of the fixed analyzer; and a controller configured to generate a pulse controlling the first hollow shaft stepping motor and the fourth hollow shaft stepping motor and information determining a rotation speed of the second hollow shaft constant speed rotation motor and a rotation speed of the third hollow shaft constant speed rotation motor and control an operation of the respective components.

The achromatic rotating-element ellipsometer may further include: an operator configured to calculate a Mueller-matrix component of the sample from a Fourier coefficient for a radiant flux waveform of light calculated from a value of the radiant flux of the light output from the photodetector, wherein the constant speed rotation polarizer may rotate at a predetermined multiple of a reference angular velocity, the constant speed rotation analyzer may rotate at another predetermined multiple of the reference angular velocity, and the photodetector may at least output the value of the radiant flux of the light for a rotation period of the reference angular velocity.

The achromatic rotating-element ellipsometer may further include: a storage unit configured to store the Fourier coefficient and the Mueller-matrix component; and a display unit configured to display the Mueller-matrix component.

An Equation for the exposure is $S_j = \int_{(j-1)T/J+T_d}^{(j-1)T/J+T_d+T_i} I(t)dt$, (j=1, ..., J), and average values of the Fourier coefficient of the radiant flux waveform of the light may be $$\langle I'_0 \rangle = \frac{\langle H_0^c \rangle}{2T_i},$$

$$\langle A'_n \rangle = C_n^c \langle H_n^c \rangle - C_n^s \langle H_n^s \rangle, (n \geq 1),$$

$$\langle B'_n \rangle = C_n^c \langle H_n^s \rangle + C_n^s \langle H_n^c \rangle, (n \geq 1),$$

$$C_n^c = \frac{\xi_n}{T_i \sin \xi_n} \cos\left[\xi_n\left(1 + \frac{2T_d}{T_i}\right)\right], (n \geq 1), \text{ and}$$

$$C_n^s = \frac{\xi_n}{T_i \sin \xi_n} \sin\left[\xi_n\left(1 + \frac{2T_d}{T_i}\right)\right], (n \geq 1).$$

Here, $$\left(I(t) = I'_0 + \sum_{n=1}^{N_{ho}} [A'_n \cos(n\omega t) + B'_n \sin(n\omega t)]\right):$$

Radiant flux waveform of light, $\omega(=2\pi/T)$: Reference angular velocity of constant speed rotation optical elements, $T(=2\pi/\omega)$: Rotation period for reference angular velocity, $I_0'$: Direct current (dc) among Fourier coefficient components of radiant flux waveform of light, $A'_n$, $B'_n$: Alternating current (ac) components of Fourier coefficient components of radiant flux waveform of light, $N_{ho}$: Largest index value among nonzero Fourier coefficient components, J: The number of exposure sets measured for rotation time T, $T_i$: Integration time, $T_d$: Delay time, $$\langle H_n^c \rangle + i \langle H_n^s \rangle = \frac{2}{NJ} \sum_{j=1}^{NJ} S_j \exp\left[i\frac{2n\pi(j-1)}{J}\right],$$

N: Measurement repetitive frequency of Fourier coefficient, and $\xi_n = n\pi T_i/T$).

The Equation for the exposure may be $S_j = \int_{(j-1)T/J+T_d}^{(j-1)T/J+T_d+T_i} I(t)dt$, (j=1, ..., J), and corrected Fourier coefficient values of the radiant flux waveform of the light may be $I_0 = I'_0$, $A_n = A'_n \cos(n\theta_{r0,n}) + B'_n \sin(n\theta_{r0,n})$, and $B_n = A'_n \sin(n\theta_{r0,n}) + B'_n \cos(n\theta_{r0,n})$.

Here, $$\left(I(\theta_r) = I_0 + \sum_{n=1}^{N_{ho}} [A_n \cos(n\theta_r) + B_n \sin(n\theta_r)]\right):$$

Radiant flux waveform of light, $I_0$: Direct current component of corrected Fourier coefficient of radiant flux waveform of light, $T(=2\pi/\omega)$: Rotation period for reference angular velocity, $A_n$, $B_n$: Alternating current component of corrected Fourier coefficient of radiant flux waveform of light, $\theta_r$: Azimuth variation due to reference angular velocity measured for real origin, $-\theta_{r0,n}$: Value of $\theta_r$ when t=0, $\omega t = \theta_r + \theta_{r0,n}$, $N_{ho}$: Largest index value among nonzero Fourier coefficient components, J: The number of exposure sets measured for rotation period time T, $T_i$: Integration time, and $T_d$: Delay time).

The Equation for the exposure may be $S_j = \int_{(j-1)T/J+T_d}^{(j-1)T/J+T_d+T_i} I(t)dt$, (j=1, ..., J), and corrected Fourier coefficient values of the radiant flux waveform of the light may be $$I_0 = \gamma \sum_{j=1}^{u} \sum_{k=1}^{v} i_{0,jk} M_{jk} = \gamma i_0 \cdot V^{(SP)},$$

$$A_n = \gamma \sum_{j=1}^{u} \sum_{k=1}^{v} a_{n,jk} M_{jk} = \gamma a_n \cdot V^{(SP)}, \text{ and}$$

$$B_n = \gamma \sum_{j=1}^{u} \sum_{k=1}^{v} b_{n,jk} M_{jk} = \gamma b_n \cdot V^{(SP)}.$$

Here, $$\left(I(\theta_r) = I_0 + \sum_{n=1}^{N_{ho}} [A_n \cos(n\theta_r) + B_n \sin(n\theta_r)]\right):$$

Radiant flux waveform of light, $I_0$: Direct current component of corrected Fourier coefficient of radiant flux waveform of light, $A_n$, $B_n$: Alternating current component of corrected Fourier coefficient of radiant flux waveform of light, $\theta_r$: Azimuth variation due to reference angular velocity measured for real origin, $-\theta_{r0,n}$: Value of $\theta_r$ when t=0, $\omega t = \theta_r + \theta_{r0,n}$, $N_{ho}$: Largest index value among nonzero Fourier coefficient components, J: The number of exposure sets measured for rotation period time T, $T_i$: Integration time, and $T_d$: Delay time), $V^{(SP)} = (M_{11}, \ldots, M_{1v}, \ldots, M_{u1}, \ldots, M_{uv})^T$: Solution by which Mueller-matrix component for the sample is represented by vector, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_n=(\partial B_n/\partial M_{11}, \ldots, \partial B_n/\partial M_{1v}, \ldots, \partial B_n/\partial M_{u1}, \ldots, \partial B_n/\partial M_{uv})/\gamma$, $\gamma=\kappa(1+d_{12}\cos 2A+d_{13}\sin 2A)(1+l_1\cos 2P+l_2\sin 2P)$: Common factor associated with transmittance state of optical element, P, A: Azimuth positions at real origin coordinate system of property axes of fixed polarizer and fixed analyzer, $M^{(SP)}=(M_{jk})_{4\times4}$: Mueller-matrix of sample, $\kappa=\mu_{QE}A_{PDE}T_{PSA}T_{PSG}D_{11}L_0$, $d_{12(13)}=D_{12(13)}/D_{11}$, $l_{1(2)}=L_{1(2)}/L_0$, $\mu_{QE}$: Quantum efficiency of photodetector, $A_{PDE}$: Effective measurement area of photodetector, $T_{PSG}$, $T_{PSA}$: Effective transmission coefficient of polarization state generator and polarization state analyzer, u, v: Predetermined integer differently given depending on a type of optical element rotation type spectroscopic ellipsometer used, $S^{(LS)}=(L_0, L_1, L_2, L_3)^T$: Stokes vector of light wave incident to pass through polarization state generator, $M^{(DOS)}=(D_{jk})_{4\times4}$: Mueller-matrix of detector optic system (DOS) disposed between polarization state analyzer and photodetector, PSG: Polarization state generator including fixed polarizer and constant speed rotation polarizer, and PSA: Polarization state analyzer including constant speed rotation analyzer and fixed analyzer).

The solution by which a Mueller-matrix component for the sample is represented by vector may be $$V^{(SP)}=(\Omega^T\Omega)^{-1}\Omega^T X.$$

Here, $$I(\theta_r)=I_0+\sum_{n=1}^{N_{ho}}[A_n\cos(n\theta_r)+B_n\sin(n\theta_r)]:$$

Radiant flux waveform of light, $I_0$: Direct current component of corrected Fourier coefficient of radiant flux waveform of light, $A_n$, $B_n$: Alternating current component of corrected Fourier coefficient of radiant flux waveform of light, $N_{ho}$: Largest index value among nonzero Fourier coefficient components, J: The number of exposure sets measured for rotation period time T, $T_i$: Integration time, and $T_d$: Delay time), $V^{(SP)}=(M_{11}, \ldots, M_{1v}, \ldots, M_{u1}, \ldots, M_{uv})^T$: Solution by which Mueller-matrix component for the sample is represented by vector, $X=I_0, A_1, B_1, A_2, B_2, \ldots, A_{N_{ho}}, B_{N_{ho}})^T$: Column vector of corrected Fourier coefficient, $\Omega=\gamma(i_0, a_1, b_1, a_2, b_2, \ldots, a_{N_{ho}}, b_{N_{ho}})^T$: $(2N_{ho}+1)$-by-uv coefficient matrix consisting of the row vector as component, $i_0=(\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n=(\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_n=(\partial B_n/\partial M_{11}, \ldots, \partial B_n/\partial M_{1v}, \ldots, \partial B_n/\partial M_{u1}, \ldots, \partial B_n/\partial M_{uv})/\gamma$, $\gamma=\kappa(1+d_{12}\cos 2A+d_{13}\sin 2A)(1+l_1\cos 2P+l_2\sin 2P)$: Common factor associated with transmittance state of optical element, P, A: Azimuth positions at real origin coordinate system of property axes of fixed polarizer and fixed analyzer, $M^{(SP)}=(M_{jk})_{4\times4}$: Mueller-matrix of sample, $\kappa=\mu_{QE}A_{PDE}T_{PSA}T_{PSG}D_{11}L_0$, $d_{12(13)}=D_{12(13)}/D_{11}$, $l_{1(2)}=L_{1(2)}/L_0$, $\mu_{QE}$: Quantum efficiency of photodetector, $A_{PDE}$: Effective measurement area of photodetector, $T_{PSG}$, $T_{PSA}$: Effective transmission coefficient of polarization state generator and polarization state analyzer, u, v: Predetermined integer differently given depending on a type of optical element rotation type spectroscopic ellipsometer used, $S^{(LS)}=(L_0, L_1, L_2, L_3)^T$: Stokes vector of light wave incident to pass through polarization state generator, $M^{(DOS)}=(D_{jk})_{4\times4}$: Mueller-matrix of detector optic system (DOS) disposed between polarization state analyzer and photodetector, PSG: Polarization state generator including fixed polarizer and constant speed rotation polarizer, and PSA: Polarization state analyzer including constant speed rotation analyzer and fixed analyzer).

The achromatic rotating-element ellipsometer may further include: a sample support configured to support the sample; a sample transfer apparatus configured to transfer a measurement point of the sample to another point; a sample storage vessel configured to store at least one sample; and a sample transfer apparatus configured to take one sample out from the sample storage vessel and transfer the taken out sample to the sample support.

The achromatic rotating-element ellipsometer may further include: a sample alignment system configured to align the sample to measure the exposure, in which the sample alignment system may include a laser radiating light, an optical system making the light radiated from the laser toward a predetermined direction, and a photodetector configured to receive light reflected from the sample.

The achromatic rotating-element ellipsometer may further include: a focusing optical system configured to focus a focus of the incident light on the sample; and a collimator configured to change light reflected from or transmitted through the sample to parallel light again.

The light source may be any one selected from a xenon lamp, a tungsten-halogen lamp, a deuterium lamp, a gas laser, a laser diode, and an apparatus transmitting light radiated therefrom through an optical fiber.

The photodetector may include a CCD, CMOS, or photodiode element, and pixels including a plurality of CCDs, CMOS s, or photodiode elements may be arranged in a linear or two-dimensional plane structure.

The photodetector may be a single photodetector including photomultiplier tubes or a photodiode.

The photodetector may include a cooling apparatus.

A method for measuring Mueller-matrix of a sample using the achromatic rotating-element ellipsometer including: a sample mounting step (S10) of mounting the sample; an azimuth selecting step (S20) of selecting set azimuths of a fixed polarizer and a fixed analyzer, respectively; an azimuth moving step (S30) of moving each azimuth of the fixed polarizer and the fixed analyzer to the set azimuths; an exposure measuring step (S40) of measuring an exposure of incident light depending on a change in azimuths of a constant speed rotation polarizer and a constant speed rotation analyzer and outputting a value of a radiant flux of light from the exposure; a Fourier coefficient calculating step S50 of calculating Fourier coefficients of a radiant flux waveform of the light from the value of the radiant flux of the light; and a Mueller-matrix calculating step (S60) of calculating Mueller-matrix components of the sample from the Fourier coefficients.

Advantageous Effects

As described above, according to the exemplary embodiment of the present invention, it is possible to provide the achromatic rotating-element ellipsometer and the method for measuring Mueller-matrix elements of a sample using the same capable of measuring the Mueller-matrix elements of the anisotropic sample as well as the isotropic sample by using four polarizers.

Accordingly, it is possible to more quickly measure the shape and physical properties of the anisotropic sample as compared with the ellipsometer for measuring the shape and physical properties of the sample and the measuring method using the same according to the related art.

BEST MODE

Figure 1:
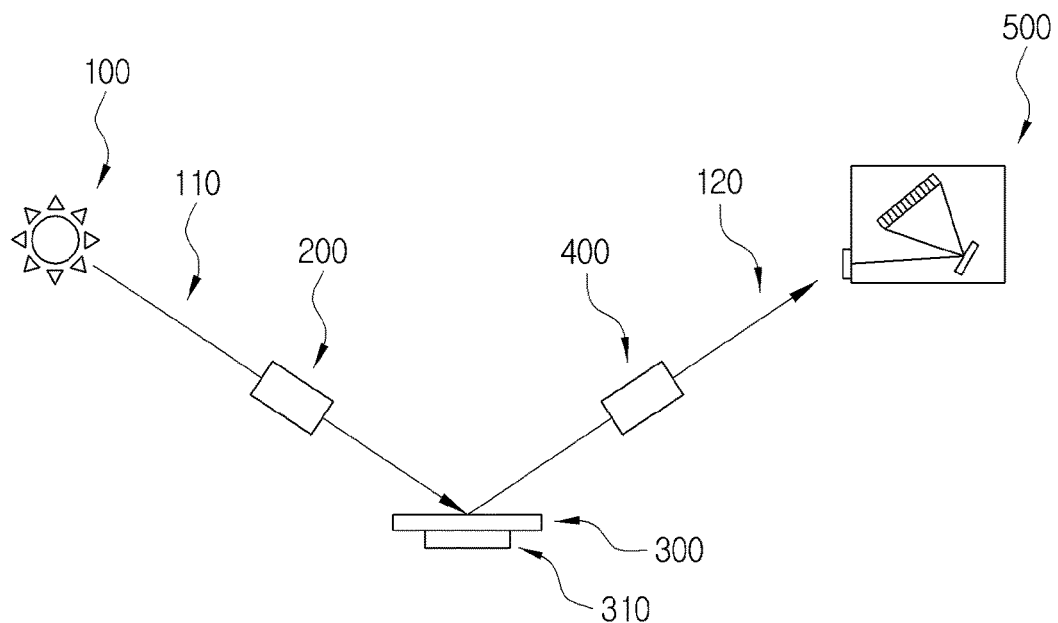
FIG. 1 is a diagram schematically illustrating the existing optical element rotation type Mueller-matrix ellipsometer.

The description of the invention is merely an example for structural or functional explanation, and therefore the scope of the present invention should not be construed as being limited by the embodiments described herein. That is, the embodiments can be variously embodied and have various forms, and therefore the scope of the present invention should be understood as including equivalents capable of realizing technical ideas.

Meanwhile, the meaning of the terms described in the present application should be understood as follows.

The terms first, second, etc. are intended to distinguish one element from another and therefore the scope of the present invention should not be limited by these terms. For example, the 'first' component may be named the 'second' component, and vice versa.

It is to be understood that when one element is referred to as being "at upper part" or "on" of another element, it may be just on another element, and may also have the other element intervening therebetween. On the other hand, it is to be understood that when one element is referred to as "contact" another element, the other element is not present therebetween. Meanwhile, other expressions describing a relationship between components, that is, "intervening", "directly intervening", "between", "directly between", "neighboring to", "directly neighboring to" and the like, should be similarly interpreted.

It will be further understood that the singular expression should be understood as including the plural expression unless the context clearly dictates otherwise, the terms "comprises" or "have" used in this specification, specify the presence of stated features, numerals, steps, operations, components, parts, or a combination thereof, but do not preclude the presence or addition possibility of one or more other features, numerals, steps, operations, components, parts, or a combination thereof.

Therefore, the respective steps may be performed in a sequence different from a described sequence unless the context clearly defines a specific sequence. That is, the respective steps may be performed in the same sequence as the described sequence, be performed at substantially the same time, or be performed in an opposite sequence to the described sequence.

The drawings referred to for explaining embodiments of the present disclosure are exaggerated in size, height, thickness, and the like intentionally for convenience of explanation and understanding, and are not enlarged or reduced according to a proportion. In addition, any of the components shown in the drawings may be intentionally reduced, and other components may be intentionally enlarged.

All terms used herein have the same meaning as commonly understood by one of ordinary skill in the art to which the present invention belongs, unless otherwise defined. It must be understood that the terms defined in the dictionary generally used are identical with the meanings within the context of the related art, and they should not be ideally or excessively formally defined unless the context clearly dictates otherwise.

Figure 2:
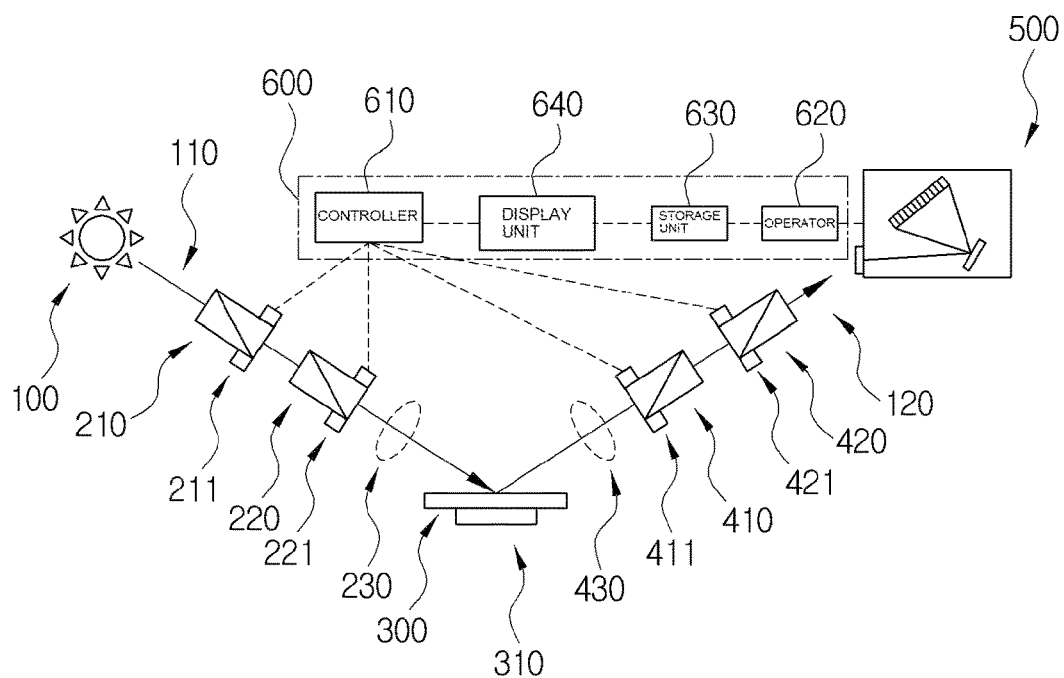
FIG. 2 is a diagram schematically illustrating an achromatic rotating-element ellipsometer according to an exemplary embodiment of the present invention.

Hereinafter, an achromatic rotating-element ellipsometer and a method for measuring Mueller-matrix elements of a sample using the same according to an exemplary embodiment of the present invention will be described with reference to the accompanying drawings. FIG. 1 is a diagram schematically illustrating the existing optical element rotation type Mueller-matrix ellipsometer and FIG. 2 is a diagram schematically illustrating an achromatic rotating-element ellipsometer according to an exemplary embodiment of the present invention.

Referring to FIG. 1, the existing optical element rotation type ellipsometer may include a light source 100, a polarization state generator 200, a sample 300, a polarization state analyzer 400, and a photodetector 500. The main components of the existing optical element rotation type Mueller-matrix ellipsometers may be the light source 100, the polarization state generator 200 that is an optical system for changing light emitted from the light source into a specific polarization state, the sample 300 that is disposed on a progress path of modulated incident light, the polarization state analyzer 400 that is an optical system for analyzing the polarization state of reflected light (or transmitted light) on a progress path of the light reflected from (transmitted through) the sample, and a photodetector 500 that measures a light quantity of the light passing through the polarization state analyzer as values such as a voltage and a current.

The polarization state generator or the polarization state analyzer may include a plurality of rotatable optical elements appropriately arranged therein according to a type of ellipsometers, in which the rotatable optical element may include linear polarizers and compensating elements, the rotatable optical elements selected from the rotatable optical elements rotate at a constant velocity, and the remaining rotatable optical elements except for the constant velocity optical elements are a fixed optical element and may move to a predetermined azimuth for measurement and stop upon the measurement.

The existing most commonly used Mueller-matrix ellipsometers are a dual-optical element rotation type ellipsometer in which two optical elements have a constant velocity ratio and rotate at a constant velocity, and may include, for example, a dual-compensating element rotation type ellipsometer, a rotation-compensating element rotation-analyzer ellipsometer, a rotation-polarizer rotation-compensating element ellipsometer, and a rotation-polarizer rotation-analyzer ellipsometer.

The principle of the optical element rotation type ellipsometer is that incident light emitted from the light source 100 is incident on the polarization state generator, the incident light is changed to a specific polarization state that may be controlled by the polarization state generator 200, the incident light modulated into the polarization state is irradiated to the sample 300 and thus the polarization state of the incident light is changed by the sample 300 so that the incident light becomes reflected light (or transmitted light) having physical properties information of the sample, the reflected light (or transmitted light) is incident on the polarization state analyzer 400 to be changed to the specific polarization state which may be controlled once more, and the reflected light suffering from the series of changes is measured using the photodetector 500, such that the reflected light is comprehensively reconstructed to have the physical properties information of the sample 300.

Referring to FIG. 2, the optical element rotation type Mueller-matrix ellipsometer according to the exemplary embodiment of the present invention may include the light source 100, a fixed polarizer 210, a first hollow shaft stepping motor 211, a constant velocity rotation polarizer 220, a second hollow shaft constant velocity rotation motor 221, a focusing optical system 230, the sample 300, a sample support 310, a collimator 430, a fixed analyzer 410, a third hollow shaft constant velocity rotation motor 411, a constant velocity rotation analyzer 420, a fourth hollow shaft stepping motor 421, the photodetector 500, a controller 610, an operator 620, a storage unit 630, and a display unit 640 all of which are disposed on an incident light path. In this configuration, the fixed polarizer 210, the first hollow shaft stepping motor 211, the constant velocity rotation polarizer 220, the second hollow shaft constant velocity rotation motor 221, and the focusing optical system 230 are components configuring the polarization state generator 200. In addition, the collimator 430, the fixed analyzer 410, the third hollow shaft constant velocity rotation motor 411, the constant velocity rotation analyzer 420, and the fourth hollow shaft stepping motor 421 are components configuring the polarization state analyzer 400. In this configuration, the controller 610, the operator 620, the storage unit 630, and the display unit 640 may be implemented using the computer 600.

The light source 100, an incident light 110 that is emitted in parallel from the light source 100 toward the sample, the fixed polarizer 210 that is placed between the incident light and the sample to stop at a specified azimuth upon measurement and make the passed incident light into a linear polarization state in a specific direction, the constant velocity rotation polarizer 220 that is disposed between the fixed polarizer and the sample and rotates at a constant velocity upon measurement to modulate the polarization state of light passing through the fixed polarizer, the light passing through the constant velocity rotation polarizer being reflected (or transmitted through) from the sample so that the polarization state thereof is changed, the constant velocity rotation analyzer 410 that is disposed between the sample 300 and the photodetector to rotate at a constant velocity having a ratio different from that of constant velocity rotation polarizer upon the measurement in order to analyze the polarization state changed by the sample of the reflected light (or transmitted light) on the reflected light (or transmitted light) line, the fixed analyzer 420 that is disposed between the constant velocity rotation analyzer and the photodetector and stops at the specified azimuth upon the measurement to pass only the linear polarization component in the specific direction of the light passing through the constant velocity rotation analyzer; and the photodetector 500 that measures an exposure amount of the light passing through the fixed analyzer and outputs a value of a radiant flux of the light corresponding thereto may be disposed on the incident light line.

In addition, the controller 610 that may control the azimuths of the fixed polarizer 210 and the fixed analyzer 420 using the hollow shaft stepping motors 211 and 421 and remotely control the rotation velocities of the constant velocity rotation polarizer 220 and the constant velocity rotation analyzer 410 using the constant velocity rotation motors 221 and 411, the operator 620 that calculates a Fourier coefficient for a radiant flux waveform from the values of the radiant flux of the light measured by the photodetector 500 and calculates the Mueller-matrix components for the sample from the Fourier coefficient values, the storage unit 630 that stores the calculated values of the Fourier coefficients for the radiant flux waveform and the Mueller-matrix components of the sample, and the display unit 640 that may display the calculated values on a screen of a monitor if necessary may be provided.

The optical element rotation type Mueller-matrix ellipsometer according to the exemplary embodiment of the present invention may include the sample support 310 for changing the alignment and measurement position of the sample, and a sample transfer system (not illustrated) that has a sample having 6 degrees of freedom that includes parallel movement with 3 degrees of freedom of height and left and right, tilt adjustment with 2 degrees of freedom, and a rotation function may be mounted on one surface of the sample support.

In the case of the semiconductor industry, the optical element rotation type Mueller-matrix ellipsometer according to the exemplary embodiment of the present invention is important to measure a plurality of wafer samples within a rapid time. To this end, the optical element rotation type Mueller-matrix ellipsometer may include a sample storage vessel (not illustrated) that may store samples and a sample transfer apparatus (not illustrated) that sequentially takes out the samples one by one from the sample storage vessel to measure physical properties of the samples, transfers the taken out samples to the sample support, and transfers the samples located on the sample support to a sample storage box if the measurement is completed at designated points.

The optical element rotation type Mueller-matrix ellipsometer according to the present invention may include a sample alignment system (not illustrated) that includes a laser emitting light for sample alignment to align the sample for the measurement, the optical system making the light emitted from the laser be incident on the sample in the specific direction, and the photodetector receiving the light reflected from the sample with respect to the incident light and distinguishing the location of the received light.

When used in fields such as the semiconductor industry, the optical element rotation type Mueller-matrix ellipsometer according to the exemplary embodiment of the present invention may selectively include the focusing optical system 230 installed in a front path of the sample to focus incident light on a local area of the sample because a size of an area to be measured in a sample is very small as tens of micrometers and the collimator 430 changing light reflected from or transmitted through the sample to parallel light again.

Here, the focusing optical system 230 and the collimator 430 may include an optical system that includes one or more mirrors, include one or more lenses made of heterogeneous materials, or one or more mirrors and one or more lenses in order to correct chromatic aberration for a wide band wavelength, and may use the lenses or the mirrors coated with a single thin film or a multilayer thin film in order to improve transmission or reflection efficiency.

In the optical element rotation type Mueller-matrix ellipsometer according to the present invention, the light source 100 may be any one selected from a xenon lamp, a tungsten-halogen lamp, a deuterium lamp, a gas laser, a laser diode, and an apparatus transmitting light radiated therefrom through an optical fiber. Such light source devices may have a residual polarization characteristic in which intensity of light polarized in a certain direction is relatively larger than that of light polarized in the other direction, but may be advantageous in generating light of a specific wavelength.

The photodetector 500 of the optical element rotation type Mueller-matrix ellipsometer according to the exemplary embodiment of the present invention may include, as a component, one pixel or one selected from several pixels binned in a spectrometer including a charge coupled device (CCD), CMOS, or photodiode (PD) array element, with the pixels being arranged in a linear structure or a two-dimensional plane structure. Further, the photodetector 500 may include, as a component, one selected from single photodetectors including a PMT, a photodiode, or the like.

The photodetector remains in a standby state before an external trigger is transmitted. Then, the photodetector may measure an exposure for an integration time specified for each pixel of the photodetector if the external trigger is transmitted and output or temporarily store a value of a radiant flux of light corresponding to the measured value. At this point, an integrating photodetector using the CCD, CMOS, or photodiode array element may output or temporarily store the exposure value for the integration time specified for each pixel of the photodetector, and a non-integrating photodetector such as the single photodetector including the PMT, the photodiode, or the like may approximately output or temporarily store an exposure value for a very short period of time, that is, a value of a radiant flux of light.

In order to decrease an error due to a change in a measurement environment, the photodetector of the optical element rotation type Mueller-matrix ellipsometer according to the exemplary embodiment of the present invention may include an apparatus allowing a light path to be in an atmosphere state such as nitrogen gate, argon gas, or the like, for measurement for a wide band wavelength, in which the ellipsometer may be installed on a damping system in order to decrease an influence due to vibrations of a system and a measurement environment, and may include a constant temperature system for decreasing a measurement error due to a temperature change with respect to the light source, the optical elements, the sample, and the photodetector. Instead of a thermostat, a cooling device may be attached to the photodetector to reduce the temperature-dependent measurement error.

Figure 3:
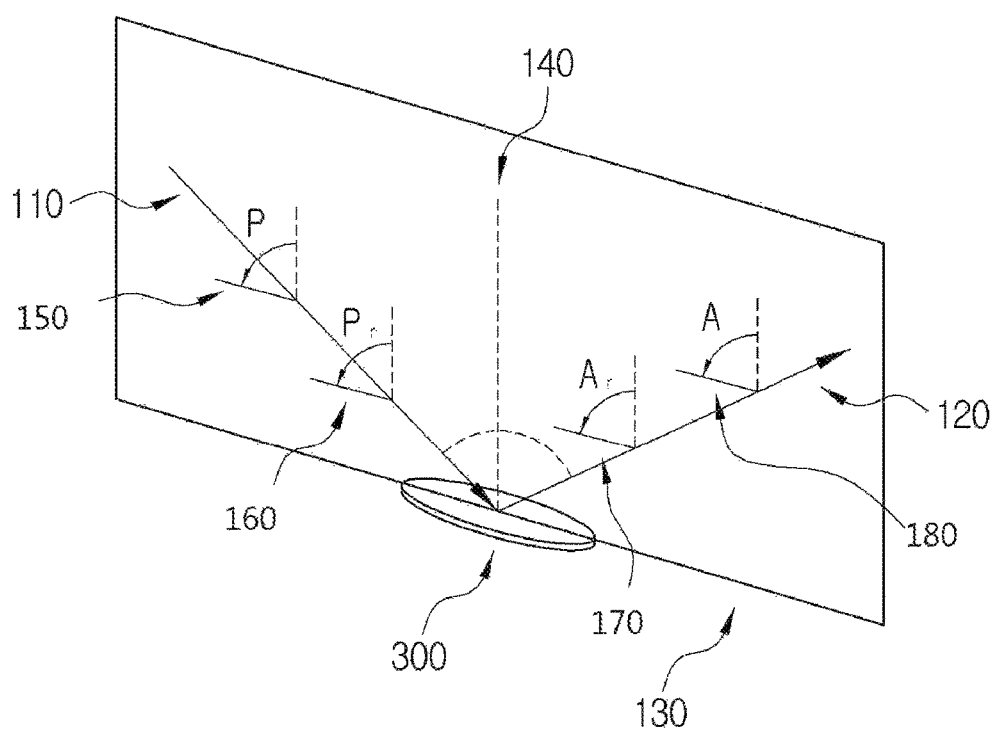
FIG. 3 is a conceptual diagram for describing the respective azimuths for a fixed polarizer, a constant velocity rotation polarizer, a constant velocity rotation analyzer, and a fixed analyzer used in the achromatic rotating-element ellipsometer according to an exemplary embodiment of the present invention.

FIG. 3 is a conceptual diagram for describing the respective azimuths for a fixed polarizer, a constant speed rotating polarizer, a constant speed rotation analyzer, and a fixed analyzer used in the achromatic rotating-element ellipsometer according to an exemplary embodiment of the present invention. Referring to FIG. 3, among planes perpendicular to a surface of the sample, a surface on which a path of the incident light 110 having an incident angle ϕ and a path of the reflected light 120 having a reflected angle ϕ are present will be defined as an incident surface 130 and an axis perpendicular to the sample 200 will be defined as a reference axis 140. As illustrated in FIG. 3, azimuths for a transmitting axis direction 150 of a linear polarizer in the fixed polarizer, a transmitting axis direction 160 of a linear polarizer in the constant speed rotation polarizer, a transmitting axis direction 170 of a linear polarizer in the constant speed rotation analyzer, and a transmitting axis direction 180 of a linear polarizer in the fixed polarizer are measured based on the incident surface 130 and are generally represented by P, $P_r$, $A_r$, and A, respectively.

Any radiant flux waveform function $I_{ex}$ (t) which is a period T($=2\pi/\omega$) is a function of time (t) and is expressed by the following Equation (1).

$$I_{ex}(t) = I'_0 + \sum_{n=1}^{N_{ho}} [A'_n \cos(n\omega t) + B'_n \sin(n\omega t)] \quad (1)$$

In the above Equation (1), $I_0'$ represents a direct current (dc) component among Fourier coefficient components of the radiant flux waveform, $A'_n$ and $B'_n$ represent alternating current (ac) components among Fourier coefficient components of the radiant flux waveform, ω represents a reference angular velocity of the constant speed rotation optical element, and $N_{ho}$ represents the largest index value among nonzero Fourier coefficient components.

Therefore, in the ideal optical element rotation type Mueller-matrix ellipsometer without errors, the radiant flux value at a monochromatic wavelength to be measured by the photodetector in time can be expressed by the following general waveform Equation.

$$I(t) = I'_0 + \sum_{n=1}^{N_{ho}} [A'_n \cos(n\omega t) + B'_n \sin(n\omega t)] \quad (2)$$

In the above Equation (2), $I_0'$ represents the direct current component of the Fourier coefficient, $A'_n$ and $B'_n$ represent the alternating current components of the Fourier coefficient, $\omega(=2\pi/T)$ represents the reference angular velocity of the optical element rotating at a constant speed, and $N_{ho}$ represents the largest index value among the nonzero alternating current components of the Fourier coefficient. In the optical element rotation type Mueller-matrix ellipsometer according to the exemplary embodiment of the present invention, the angular velocity of the constant speed rotation polarizer is $m_P\omega$ which is constant $m_P$ times the reference angular velocity ω, and the angular velocity of the constant speed rotation analyzer may be $m_A\omega$ which is constant $m_A$ times the reference angular velocity ω.

In the optical element rotation type Mueller-matrix ellipsometer, it is very important to accurately measure the Fourier coefficients of the radiant flux waveform using the photodetector. In the state-of-the-art real-time optical element rotation type Mueller-matrix ellipsometer, the CCD or PD array which can collect the spectrum of Fourier coefficients as fast as possible for real-time measurement has been used as the photodetector.

The CCD or PD array has relatively excellent measurement sensitivity against weak light, such that the measurement can be made at a shorter time for a defined light quantity. Each pixel or the respective binning pixel groups of the CCD or PD array serve as the photodetector. An output signal of the CCD or PD array is in proportion to the radiant flux and the integration time and therefore the CCD or PD array is called an integrating photodetector.

The data measurement process of the CCD or the PD array can be classified into a frame acquisition process and a frame reading process. One reference pulse may be generated per the measurement period, that is, one rotation by the reference angular velocity in the constant speed rotation optical element system rotating at a constant speed, i.e., a rotation period $T(=2\pi/\omega)$ with respect to the reference angular velocity and J constant clock pulses may be generated at an equal interval of $T/J$. The reference pulse is a reference time informing the starting of the measurement by the ellipsometer and the constant clock pulse may be transferred as the external trigger for controlling the data measurement by the CCD or PD array. After the constant clock pulse is transferred to the CCD or PD array as the external trigger, the detailed process of the data measurement by the CCD or PD array for the time of the period T may be progressed in a series of order as follows. If one photodetector element in each pixel or each binning pixel group of the CCD or PD array performs a process of measuring an exposure which stores, as photoelectrons, photons of incident light for the integration time $T_i$ after a time delay for $T_d$, prior to starting the exposure after receiving the constant clock pulse as the external trigger and then performs the frame acquisition process for converting the measured exposure into an electrical signal or the value of the radiant flux of light corresponding to the exposure, there is a standby time waiting to receive the next constant clock pulse. Therefore, the measured exposure data may be expressed by the integration of the next waveform.

$$S_j = \int_{(j-1)T/J+T_d}^{(j-1)T/J+T_d+T_i} I(t)dt, \ (j=,\ldots,J) \quad (3)$$

The exposure Equation measured based on the above Equations (2) and (3) is derived to the following form.

$$S_j = T_i I'_0 + \sum_{n=1}^{N_{ho}} \frac{T_i}{\xi_n} \sin\xi_n \cos\left[\frac{2n\pi(j-1)}{J}\right]\left\{A'_n\cos\left[\xi_n\left(1+\frac{2T_d}{T_i}\right)\right] + B'_n\sin\left[\xi_n\left(1+\frac{2T_d}{T_i}\right)\right]\right\} - \sum_{n=1}^{N_{ho}} \frac{T_i}{\xi_n} \sin\xi_n \sin\left[\frac{2n\pi(j-1)}{J}\right]\left\{A'_n\sin\left[\xi_n\left(1+\frac{2T_d}{T_i}\right)\right] - B'_n\cos\left[\xi_n\left(1+\frac{2T_d}{T_i}\right)\right]\right\} \quad (4)$$

In the above Equation (4), $o_n=n\pi T_i/T$. In the above Equation (4), J exposure sets measured for the time T form a group of a linear Equation consisting of $2N_{ho}+1$ unknown Fourier coefficients of the above Equation (2), which may be simply expressed by $S=\Xi X'$. Here, $S=(S_1, \ldots, S_J)^T$ representing the exposure and $X'=(I'_0, A'_1, B'_1, \ldots, A'_{N_{ho}}, B'_{N_{ho}})^T$ representing the Fourier coefficients are a column vector and $\Xi$ is a coefficient matrix of J-by-$(2N_{ho}+1)$. If a least squares method is used in a case where J is one of elements of a union of integer sets of $\{J \geq 2N_{ho}+1, \text{ for odd } J\}$ and $\{J \geq 4N_{ho}+2, \text{ for even } J\}$, a solution to calculate a Fourier coefficient X' from the exposure S like $X'=(\Xi^T\Xi)^{-1}\Xi^T S$ can be obtained.

A new principle of applying a discrete Fourier transform to the exposures measured depending on the above Equation (4) has been developed. The result is the same as the result obtained by the least squares method but the expression method thereof may be simpler as follows.

$$\langle H_n^c \rangle + i\langle H_n^s \rangle = \frac{2}{NJ}\sum_{j=1}^{NJ} S_j \exp\left[i\frac{2n\pi(j-1)}{J}\right] \quad (5)$$

In the above Equation (5), $\langle H_n^c \rangle$ and $\langle H_n^s \rangle$ are a real-valued function and angle brackets represent an average value for measurement values obtained by performing a measurement in a total of N times when the measurement is performed once every rotation period of the reference angular velocity. Arranging the above Equation by substituting the above Equation (4) into the above Equation (5) and using orthogonality of a trigonometric function system, the average values of the measured Fourier coefficients may be obtained as follows.

$$\langle I'_0 \rangle = \frac{\langle H_0^c \rangle}{2T_i} \quad (6)$$

$$\langle A'_n \rangle = C_n^c \langle H_n^c \rangle - C_n^s \langle H_n^s \rangle, \ (n \geq 1) \quad (7)$$

$$\langle B'_n \rangle = C_n^c \langle H_n^s \rangle + C_n^s \langle H_n^c \rangle, \ (n \geq 1) \quad (8)$$

$$C_n^c = \frac{\xi_n}{T_i \sin\xi_n}\cos\left[\xi_n\left(1+\frac{2T_d}{T_i}\right)\right], \ (n \geq 1) \quad (9)$$

$$C_n^s = \frac{\xi_n}{T_i \sin\xi_n}\sin\left[\xi_n\left(1+\frac{2T_d}{T_i}\right)\right], \ (n \geq 1) \quad (10)$$

In the typical ellipsometer configuration, if the parallel light radiated from the light source passes through a polarization state generator (PSG) and is reflected from (or transmitted through) the sample and then passes through a polarization state analyzer (PSA) to be incident on the photodetector element, the radiant flux is converted into the electrical signal. The rotatable optical elements used in the optical element rotation type spectroscopic ellipsometer are divided into a polarizer, an analyzer, and a compensator, and differently arranged in the polarization state generator and the polarization state analyzer depending on the type of optical element rotation type spectroscopic ellipsometers. At least one of the rotatable optical elements in the optical element rotation type spectroscopic ellipsometer needs to rotate at a constant speed with a constant angular vibration and other rotatable optical elements each stop at the designated position. The azimuths of the rotatable optical elements may be adjusted remotely by a hollow shaft motor and if the rotatable optical elements are positioned at an azimuth reference point, that is, an index origin of the hollow shaft motor, property axes of the rotatable optical elements may be at different positions. For proper measurement, each of the azimuth positions of the property axes of the optical elements which are parallel to the incident surface and are rotatable from a real origin perpendicular to the sample surface needs to be found. If a calibration already well known is used, the azimuth positions of the property axes of the optical elements may be each found at a real origin coordinate system. Therefore, the above Equation (2) is transformed on the real origin coordinate system and thus is given as follows.

$$I(\theta_r) = I_0 + \sum_{n=1}^{N_{ho}} [A_n \cos(n\theta_r) + B_n \sin(n\theta_r)] \quad (11)$$

In the above Equation 11, $\theta_r$ represents an azimuth variation due to the reference angular velocity measured with respect to the real origin, $I_0$ represents the direct current components of corrected Fourier coefficients, and $A_n$ and $B_n$ are the alternating current components of the corrected Fourier coefficients. In the above Equation (11), if the azimuth is expressed by $\omega t = \theta_r + \theta_{ro,n}$, $-\theta_{ro,n}$ becomes a value of $\theta_r$ when $t=0$ and the relational Equation between the unprimed and corrected Fourier coefficients is given as follows from an identity relational Equation between the above Equations (2) and (11).

$$I_0 = I_0' \quad (12)$$

$$A_n = A'_n \cos(n\theta_{ro,n}) + B'_n \sin(n\theta_{ro,n}) \quad (13)$$

$$B_n = A'_n \sin(n\theta_{ro,n}) + B'_n \cos(n\theta_{ro,n}) \quad (14)$$

In the ellipsometer, since a data reduction function is used to extract polarization ellipsometric parameters of the sample from the corrected Fourier coefficients, it is very important to find a data reduction method suitable for the optical element rotation type spectroscopic ellipsometer. According a stokes expression, a stokes vector of a light wave to be incident to pass through the polarization state generator is set to be $S^{(LS)} = (L_0, L_1, L_2, L_3)^T$, the Mueller-matrix of the sample is represented by $M^{(SP)} = (M_{jk})_{4 \times 4}$, and the Mueller-matrices of the polarization state generator and the polarization state analyzer are represented by $T_{PSG} M^{(PSG)}$ and $T_{PSA} M^{(PSA)}$, respectively, in which TPSG and TPSA each represent effective transmission coefficients of the polarization state generator and the polarization state analyzer, $M^{(DOS)} = (D_{jk})_{4 \times 4}$ is a Mueller-matrix of a detector optic system (DOS) disposed between the polarization state analyzer and the photodetector, and finally, $S^{(PDE)} = S_0^{(PDE)}$, $S_1^{(PDE)}, S_2^{(PDE)}, S_3^{(PDE)})^T$ is the stokes vector of the light wave incident on the photodetector. The azimuth positions of the property axes of the fixed polarizer, the constant speed rotation polarizer, the constant speed rotation analyzer, and the fixed analyzer which are disposed in the polarization state generator and the polarization state analyzer are represented by P, $P_r$, $A_r$, and A in the real origin coordinate system, and the changes in the azimuth angles are each described by the Mueller-matrices for the rotation of the coordinate system.

The stokes vector of the light wave incident on the photodetector element with respect to the quasi-monochromatic light wave may be described as follows.

$$S^{(PDE)} = T_{PSA} T_{PSG} M^{(DOS)} M^{(PSA)} M^{(SP)} M^{(PSG)} S^{(LS)} \quad (15)$$

When an effective measurement area of the photodetector is represented by $A_{PDE}$ and a quantum efficiency of the photodetector is represented by $\mu_{QE}$, the radiant flux measured by the photodetector is represented by $I(\theta_r) = \mu_{QE} A_{PDE} S_0^{(PDE)}$ and solutions to the corrected Fourier coefficients obtained by the relational Equation are each given as simultaneous linear Equations for the Mueller-matrix components of the sample. To more simply represent the simultaneous linear Equations, the column vector having the Mueller-matrix components for the sample like $V^{(SP)} = (M_{11}, \ldots, M_{1v}, \ldots, M_{u1}, \ldots, M_{uv})^T$ is introduced. Here, u and v are integers differently given depending on a kind of optical element rotation type spectroscopic ellipsometers used. Therefore, the corrected Fourier coefficients are given by a scalar product as follows.

$$I_0 = \gamma \sum_{j=1}^{u} \sum_{k=1}^{v} i_{0,jk} M_{jk} = \gamma i_0 \cdot V^{(SP)} \quad (16)$$

$$A_n = \gamma \sum_{j=1}^{u} \sum_{k=1}^{v} a_{n,jk} M_{jk} = \gamma a_n \cdot V^{(SP)} \quad (17)$$

$$B_n = \gamma \sum_{j=1}^{u} \sum_{k=1}^{v} b_{n,jk} M_{jk} = \gamma b_n \cdot V^{(SP)} \quad (18)$$

In the above Equations,
$i_0 = (\partial I_0 / \partial M_{11}, \ldots, \partial I_0 / \partial M_{1v}, \ldots, \partial I_0 / \partial M_{u1}, \ldots, \partial I_0 / \partial M_{uv}) / \gamma$,
$a_n = (\partial A_n / \partial M_{11}, \ldots, \partial A_n / \partial M_{1v}, \ldots, \partial A_n / \partial M_{u1}, \ldots, \partial A_n / \partial M_{uv}) / \gamma$, and
$b_n = (\partial B_n / \partial M_{11}, \ldots, \partial B_n / \partial M_{1v}, \ldots, \partial B_n / \partial M_{u1}, \ldots, \partial B_n / \partial M_{uv}) / \gamma$
are generally a function of only the azimuth of the fixed optical elements, but are a function that further includes the azimuth and the retardation angle of the compensator if the compensator is included and are described by a row vector. Here, $\gamma$ is a common factor that is associated with the intensity and the polarization characteristics of the light source, the effective measurement area and quantum efficiency of the photodetector, the polarization dependent characteristics of the DOS, and the transmittance state of the optical element used in the optical element rotation type spectroscopic ellipsometer, which is given as follows.

$$\gamma = \kappa(1 + d_{12} \cos 2A + d_{13} \sin 2A)(1 + l_1 \cos 2P + l_2 \sin 2P) \quad (19)$$

Here, $\kappa = \mu_{QE} A_{PDE} T_{PSA} T_{PSG} D_{11} L_0$, $d_{12(13)} = D_{12(13)}/D_{11}$, and $l_{1(2)} = L_{1(2)}/L_0$.

The solution of the simultaneous linear Equations depending on the total number of linear Equations used for the data reduction is given in a unique or overdetermined form. The present research introduces a generalized data reduction method which may be applied to all the types of optical element rotation type spectroscopic ellipsometer and may obtain the ellipsometric parameters of the sample from all the Fourier coefficients. If the column vector of the corrected Fourier coefficients is expressed by $X = I_0, A_1, B_1, A_2, B_2, \ldots, A_{N_{ho}}, B_{N_{ho}})^T$ and the $(2N_{ho}+1)$-by-uv coefficient matrix consisting of the row vector as the component is expressed by $\Omega = \gamma(i_0, a_1, b_1, a_2, b_2, \ldots, a_{N_{ho}}, b_{N_{ho}})^T$, equation (16)~(18) may be represented by $X = \Omega V^{(SP)}$. If a matrix rank of $\Omega$ is equal to or larger than a total number of unknown matrix elements in $M^{(SP)}$, a solution of the vector for the Mueller-matrix components for the sample is given as follows.

$$V^{(SP)} = (\Omega^T \Omega)^{-1} \Omega^T X \quad (20)$$

Therefore, if values of $\kappa$, $d_{12}$, $d_{13}$, $l_1$ and $l_2$ for each wavelength is obtained from a measurement result using the reference sample with the well known optical properties or a measurement result on a straight line without the sample based on the above Equation (19), the Mueller-matrix components of the sample may be directly calculated from the values of the corrected Fourier coefficients based on the above Equation (20). It should be emphasized herein that the solution of the vector for the Mueller-matrix component calculated in the above manner can also be applied to an anisotropic sample.

Even if the values of $\kappa$, $d_{12}$, $d_{13}$, $l_1$ and $l_2$ are unknown, it is possible to obtain the measured values of the polarization measurement parameters of the sample defined by normalized Mueller-matrix components like $m_{jk}=M_{jk}/M_{11}$. Further, in the case of the isotropic sample, generally, it may be simply represented by the polarization ellipsometric parameters of the sample defined like $N_{sp}=-m_{12}$ (or $-m_{21}$), $C_{SP}=M_{33}$ (or $m_{44}$), and $S_{SP}=m_{34}$ (or $-m_{43}$).

As described above, the radiant flux of light is measured, the optical theoretical formula for the sample is established, a plurality of unknown parameters for the region set for the established theoretical formula are used to calculate data of the Mueller-matrix components of the sample, and the least squares method, or the like is used for the data and optimizes it, thereby estimating the physical properties to be obtained from the sample. That is, it is desirable to analyze other physical characteristics from the Mueller-matrix. Accordingly, the optical element rotation type Mueller-matrix ellipsometer according to the exemplary embodiment of the present invention may analyze various physical properties such as an interface property, a thickness of a thin film, a complex refractive index, a nano shape, an anisotropic property, a surface roughness, a composition ratio, crystallinity, and the like, of the sample from the measured Fourier coefficients and the measured components of the Mueller-matrix, and may apply the analyzed results to a measurement equipment for a semiconductor element process, a measurement equipment for a flat panel display process, a measurement equipment of a solar element, a thin film optical measurement equipment, a bio sensor, a gas sensor, or the like. More specifically, in the optical element rotation type Mueller-matrix ellipsometer according to the exemplary embodiment of the present invention, when the analysis method like the nano pattern shape measurement is very complicated, the physical properties analysis method first obtains the Fourier coefficients for the sample to be measured or the measurement data of the Mueller-matrix components, establishes the optical theoretical formula for the sample, obtains data of the Fourier coefficients or the Mueller-matrix components calculated by using the plurality of unknown parameters determined in the region set for the established theoretical formula, creates a continuous function for the unknown parameters for the calculated data, and optimizes the continuous function by using the least squares method for the measurement data, thereby obtaining the physical properties of the sample. In this case, the ellipsometer according to the present invention may include a large capacity high speed calculating system configured of a high performance parallel computer, rigorous coupled-wave analysis (RCWA) algorithm based analysis software, and a large capacity data storage in order to rapidly find the physical property of the sample from the measurement data of the Fourier coefficients or the components of the Mueller-matrix measured for the sample.

Figure 4:
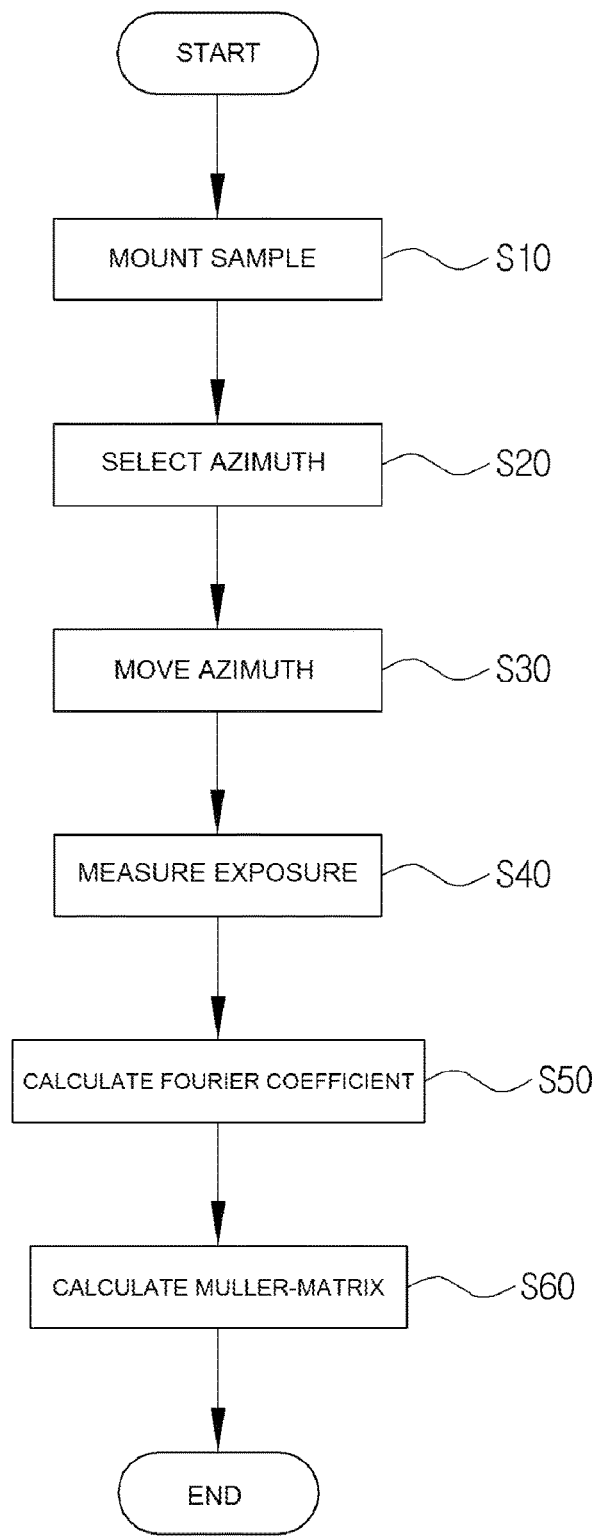
FIG. 4 is a flow chart showing a method for measuring Mueller-matrix elements of a sample using the achromatic rotating-element ellipsometer according to an exemplar embodiment of the present invention.

A method for measuring a physical property of a sample using an optical element rotation type Mueller-matrix ellipsometer according to the present invention will be described with reference to FIG. 4.

The method for measuring a physical property of a sample using an optical element rotation type Mueller-matrix ellipsometer according to the exemplary embodiment of the present invention includes a sample mounting step S10, an azimuth selecting step S20, an azimuth moving step (S30), an exposure measuring step S40, a Fourier coefficient calculating step (S50), and a Mueller-matrix calculating step S60.

The sample mounting step S10 is a step of mounting and arranging a sample of which physical properties are to be measured.

The azimuth selecting step S20 is a step of selecting azimuth values of fixed optical elements required for measurement. In the exemplary embodiment of the present invention, the set azimuth of each of the fixed polarizer and the fixed analyzer can be selected.

The azimuth moving step S30 is a step of moving the fixed optical elements to a set azimuth by a controller.

The exposure measuring step S40 is a step of measuring the exposure of the incident light according to the azimuth change of the constant speed rotation polarizer and the constant speed rotation analyzer and measuring the value of the radiant flux of light from the exposure by the photodetector.

The Fourier coefficient calculating step S50 is a step of calculating Fourier coefficients of the radiant flux waveform of light from the value of the radiant flux of light.

The Mueller-matrix storing step S60 is a step of calculating Mueller-matrix components of the sample from the Fourier coefficients.

In particular, in the exposure measuring step S40, the constant speed rotation polarizer rotates at a predetermined multiple A of the reference angular velocity and the constant speed rotation analyzer also rotates to a predetermined multiple B of the reference angular velocity. In this situation, the photodetector at least outputs the value of the radiant flux of light for a rotation period of the reference angular velocity. In this case, it may be preferable that the rotation speed of the constant speed rotation polarizer and the rotation speed of the constant speed rotation analyzer are different from each other. In other words, the predetermined multiple A for determining the rotation speed of the constant speed rotation polarizer and the predetermined multiple B for determining the rotation speed of the constant speed rotation analyzer are preferably different from each other.

While the present invention has been particularly shown and described with reference to the exemplary embodiments described and the accompanying drawings, it is to be understood by those skilled in the art that the present invention may be variously modified and changed within the technical idea of the present invention and the equivalent scope of claims to be described below.

DETAILED DESCRIPTION OF MAIN ELEMENTS

100: Light source
110: Incident light
120: Light polarized by passing through fixed analyzer
130: Incident surface
140: Incident angle reference axis
150: Direction of linear polarizer transmitting axis of fixed polarizer
160: Direction of linear polarizer transmitting axis of constant speed rotation polarizer
170: Direction of linear polarizer transmitting axis of constant speed rotation analyzer
180: Direction of linear polarizer transmitting axis of fixed analyzer
200: Polarization state generator
210: Fixed polarizer 211: First hollow shaft stepping motor
220: Constant speed rotation polarizer
221: Second hollow shaft constant speed rotation motor
230: Focusing optical system
300: Sample
310: Sample support
400: Polarization state analyzer
410: Constant speed rotation analyzer
411: Third hollow shaft constant speed rotation motor
420: Fixed analyzer
421: Fourth hollow shaft stepping motor
430: Collimator
500: Photodetector
600: Computer
610: Controller
620: Operator
630: Storage unit
640: Display unit

The invention claimed is:

1. An achromatic rotating-element ellipsometer, comprising:
a light source configured to radiate incident light toward a sample;
a fixed polarizer configured to be disposed between the light source and the sample on a travel path of the incident light and polarize the incident light radiated from the light source;
a constant speed rotation polarizer configured to be disposed between the fixed polarizer and the sample on the travel path of the incident light, have the light passing through the fixed polarizer be incident thereon, and rotate at a constant speed for polarizing the incident light;
a constant speed rotation analyzer configured to have the light polarized by passing through the constant speed rotation polarizer incident thereon and rotate at a constant speed for polarizing the incident light, with a polarization state of the light polarized by passing through the constant speed rotation polarizer being changed by being reflected from or transmitted through the sample;
a fixed analyzer configured to have the light polarized by passing through the constant speed rotation analyzer incident thereon and polarize the incident light;
a photodetector configured to have the light polarized by passing through the fixed analyzer incident thereon, detect an exposure of the incident light, and output a value of a radiant flux of light corresponding to the exposure, and
an operator configured to calculate a Mueller-matrix component of the sample from a Fourier coefficient for a radiant flux waveform of light calculated from the value of the radiant flux of the light output from the photodetector,
wherein the constant speed rotation polarizer rotates at a predetermined multiple of a reference angular velocity, the constant speed rotation analyzer rotates at another predetermined multiple of the reference angular velocity, and the photodetector at least outputs the value of the radiant flux of the light for a rotation period of the reference angular velocity,
wherein a solution by which a Mueller-matrix component for the sample is represented by vector is $V^{(SP)} = (\Omega^T \Omega)^{-1} \Omega^T X$, wherein $$I(\theta_r) = I_0 + \sum_{n=1}^{N_{ho}} [A_n \cos(n\theta_r) + B_n \sin(n\theta_r)]:$$

Radiant flux waveform of light,
$I_0$: Direct current component of corrected Fourier coefficient of radiant flux waveform of light,
$A_n$, $B_n$: Alternating current component of corrected Fourier coefficient of radiant flux waveform of light,
$N_{ho}$: Largest index value among nonzero Fourier coefficient components,
$V^{(SP)} = (M_{11}, \ldots, M_{1v}, \ldots, M_{u1}, \ldots, M_{uv})^T$: Solution by which Mueller-matrix component for the sample is represented by vector,
$X = (I_0, A_1, B_1, A_2, B_2, \ldots, A_{N_{ho}}, B_{N_{ho}})^T$: Column vector of corrected Fourier coefficient,
$\Omega = \gamma(i_0, a_1, b_1, a_2, b_2, \ldots, a_{N_{ho}}, b_{N_{ho}})^T$: $(2N_{ho}+1)$-by-uv coefficient matrix consisting of a row vector as a component,
$i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$,
$a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$,
$b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$,
$\gamma = \kappa(1+d_{12}\cos 2A+d_{13}\sin 2A)(1+l_1\cos 2P+l_2\sin 2P)$: Common factor associated with a transmittance state of an optical element,
P, A: Each azimuth positions at real origin coordinate system of property axes of fixed polarizer and fixed analyzer,
$M^{(SP)} = (M_{jk})_{4\times 4}$: Mueller matrix of sample,
$\kappa = \mu_{QE} A_{PDE} T_{PSA} T_{PSG} D_{11} L_0$,
$d_{12(13)} = D_{12(13)}/D_{11}$,
$l_{1(2)} = L_{1(2)}/L_0$,
$\mu_{QE}$: Quantum efficiency of photodetector,
$A_{PDE}$: Effective measurement area of photodetector,
$T_{PSG}$, $T_{PSA}$: Effective transmission coefficient of polarization state generator and polarization state analyzer,
u, v: Predetermined integer differently given depending on a type of optical element rotation type spectroscopic ellipsometer used,
$S^{(LS)} = (L_0, L_1, L_2, L_3)^T$: Stokes vector of light wave incident to pass through polarization state generator,
$M^{(DOS)} = (D_{jk})_{4\times 4}$: Mueller-matrix of detector optic system (DOS) disposed between polarization state analyzer and photodetector,
PSG: Polarization state generator including fixed polarizer and constant speed rotation polarizer, and
PSA: Polarization state analyzer including constant speed rotation analyzer and fixed analyzer.

2. The achromatic rotating-element ellipsometer of claim 1, further comprising:
a first hollow shaft stepping motor configured to be attached to the fixed polarizer to control an azimuth of the fixed polarizer;
a second hollow shaft constant speed rotation motor configured to be attached to the constant speed rotation polarizer to rotate the constant speed rotation polarizer at the constant speed;
a third hollow shaft constant speed rotation motor configured to be attached to the constant speed rotation analyzer to rotate the constant speed rotation analyzer at the constant speed;

a fourth hollow shaft stepping motor configured to be attached to the fixed analyzer to control an azimuth of the fixed analyzer; and a controller configured to generate a pulse controlling the first hollow shaft stepping motor and the fourth hollow shaft stepping motor and information determining a rotation speed of the second hollow shaft constant speed rotation motor and a rotation speed of the third hollow shaft constant speed rotation motor and control an operation of the respective components.

3. The achromatic rotating-element ellipsometer of claim 1, further comprising:

a storage unit configured to store the Fourier coefficient and the Mueller-matrix component; and a display unit configured to display the Mueller-matrix component.

4. The achromatic rotating-element ellipsometer of claim 1, wherein the light source is any one selected from a xenon lamp, a tungsten-halogen lamp, a deuterium lamp, a gas laser, a laser diode, and an apparatus transmitting light radiated therefrom through an optical fiber.

5. The achromatic rotating-element ellipsometer of claim 1, wherein the photodetector includes a CCD, a CMOS, or a photodiode element, and pixels including a plurality of CCDs, CMOSs, or photodiode elements are arranged in a linear or two-dimensional plane structure.

6. The achromatic rotating-element ellipsometer of claim 1, wherein the photodetector is a single photodetector including photomultiplier tubes or a photodiode.

7. A method for measuring a Mueller-matrix of a sample using the achromatic rotating-element ellipsometer of claim 1, comprising:

a sample mounting step of mounting the sample;

an azimuth selecting step of selecting set azimuths of the fixed polarizer and the fixed analyzer, respectively;

an azimuth moving step of moving each azimuth of the fixed polarizer and the fixed analyzer to the set azimuths;

an exposure measuring step of measuring the exposure of incident light depending on a change in azimuths of the constant speed rotation polarizer and the constant speed rotation analyzer and outputting a value of a radiant flux of light from the exposure;

a Fourier coefficient calculating step of calculating Fourier coefficients of the radiant flux waveform of the light from the value of the radiant flux of the light; and a Mueller-matrix calculating step of calculating Mueller-matrix components of the sample from the Fourier coefficients.

8. An achromatic rotating-element ellipsometer, comprising:

a light source configured to radiate incident light toward a sample;

a fixed polarizer configured to be disposed between the light source and the sample on a travel path of the incident light and polarize the incident light radiated from the light source;

a constant speed rotation polarizer configured to be disposed between the fixed polarizer and the sample on the travel path of the incident light, have the light passing through the fixed polarizer be incident thereon, and rotate at a constant speed for polarizing the incident light;

a constant speed rotation analyzer configured to have the light polarized by passing through the constant speed rotation polarizer incident thereon and rotate at a constant speed for polarizing the incident light, with a polarization state of the light polarized by passing through the constant speed rotation polarizer being changed by being reflected from or transmitted through the sample;

a fixed analyzer configured to have the light polarized by passing through the constant speed rotation analyzer incident thereon and polarize the incident light;

a photodetector configured to have the light polarized by passing through the fixed analyzer incident thereon, detect an exposure of the incident light, and output a value of a radiant flux of the light corresponding to the exposure; and an operator configured to calculate a Mueller-matrix component of the sample from a Fourier coefficient for a radiant flux waveform of light calculated from the value of the radiant flux of the light output from the photodetector, wherein the constant speed rotation polarizer rotates at a predetermined multiple of a reference angular velocity, the constant speed rotation analyzer rotates at another predetermined multiple of the reference angular velocity, and the photodetector at least outputs the value of the radiant flux of the light for a rotation period of the reference angular velocity, wherein an Equation for the exposure is $S_j = \int_{(j-1)T/J+T_d}^{(j-1)T/J+T_d+T_i} I(t)dt$, $(j=1, \ldots, J)$, and average values of the Fourier coefficient of the radiant flux waveform of the light are $$\langle I'_0 \rangle = \frac{\langle H_0^c \rangle}{2T_i},$$

$$\langle A'_n \rangle = C_n^c \langle H_n^c \rangle - C_n^s \langle H_n^s \rangle, \, (n \geq 1),$$

$$\langle B'_n \rangle = C_n^c \langle H_n^s \rangle + C_n^s \langle H_n^c \rangle, \, (n \geq 1),$$

$$C_n^c = \frac{\xi_n}{T_i \sin \xi_n} \cos\left[\xi_n\left(1 + \frac{2T_d}{T_i}\right)\right], \, (n \geq 1), \text{ and}$$

$$C_n^s = \frac{\xi_n}{T_i \sin \xi_n} \sin\left[\xi_n\left(1 + \frac{2T_d}{T_i}\right)\right], \, (n \geq 1), \text{ wherein}$$

$$\langle I(t) \rangle = I'_0 + \sum_{n=1}^{N_{ho}} [A'_n \cos(n\omega t) + B'_n \sin(n\omega t)];$$

Radiant flux waveform of light, $\omega(=2\pi/T)$: Reference angular velocity of constant speed rotation optical elements, $T(=2\pi/\omega)$: Rotation period for reference angular velocity, $I_0'$: Direct current (dc) component among Fourier coefficient components of radiant flux waveform of light, $A'_n, B'_n$: Alternating current (ac) components of Fourier coefficient components of radiant flux waveform of light, $N_{ho}$: Largest index value among nonzero Fourier coefficient components, J: Number of exposure sets measured for rotation period time T, $T_i$: Integration time, $T_d$: Delay time, $$\langle H_n^c \rangle + i \langle H_n^s \rangle = \frac{2}{NJ} \sum_{j=1}^{NJ} S_j \exp\left[i \frac{2n\pi(j-1)}{J}\right],$$

N: Measurement repetitive frequency of Fourier coefficient, and $o_n = n\pi T_i/T$.

9. An achromatic rotating-element ellipsometer, comprising:
- a light source configured to radiate incident light toward a sample;
- a fixed polarizer configured to be disposed between the light source and the sample on a travel path of the incident light and polarize the incident light radiated from the light source;
- a constant speed rotation polarizer configured to be disposed between the fixed polarizer and the sample on the travel path of the incident light, have the light passing through the fixed polarizer be incident thereon, and rotate at a constant speed for polarizing the incident light;
- a constant speed rotation analyzer configured to have the light polarized by passing through the constant speed rotation polarizer incident thereon and rotate at a constant speed for polarizing the incident light, with a polarization state of the light polarized by passing through the constant speed rotation polarizer being changed by being reflected from or transmitted through the sample;
- a fixed analyzer configured to have the light polarized by passing through the constant speed rotation analyzer incident thereon and polarize the incident light;
- a photodetector configured to have the light polarized by passing through the fixed analyzer incident thereon, detect an exposure of the incident light, and output a value of a radiant flux of the light corresponding to the exposure; and
- an operator configured to calculate a Mueller-matrix component of the sample from a Fourier coefficient for a radiant flux waveform of light calculated from the value of the radiant flux of the light output from the photodetector,
- wherein the constant speed rotation polarizer rotates at a predetermined multiple of a reference angular velocity, the constant speed rotation analyzer rotates at another predetermined multiple of the reference angular velocity, and the photodetector at least outputs the value of the radiant flux of the light for a rotation period of the reference angular velocity, wherein an Equation for the exposure is $S_j = \int_{(j-1)T/J+T_d}^{(j-1)T/J+T_d+T_i} I(t)dt$, $(j=1, \ldots, J)$, and corrected Fourier coefficient values of the radiant flux waveform of the light are $I_0 = I'_0$,
$A_n = A'_n \cos(n\theta_{r0,n}) + B'_n \sin(n\theta_{r0,n})$, and
$B_n = -A'_n \sin(n\theta_{r0,n}) + B'_n \cos(n\theta_{r0,n})$, wherein $$I(\theta_r) = I_0 + \sum_{n=1}^{N_{ho}} [A_n \cos(n\theta_r) + B_n \sin(n\theta_r)]:$$

Radiant flux waveform of light,
$I_0$: Direct current component of corrected Fourier coefficient of radiant flux waveform of light,
$T(=2\pi/\omega)$: Rotation period for reference angular velocity,
$A_n$, $B_n$: Alternating current component of corrected Fourier coefficient of radiant flux waveform of light,
$\theta_r$: Azimuth variation due to reference angular velocity measured for real origin, $-\theta_{r0,n}$: Value of $\theta_r$ when $t=0$,
$\omega t = \theta_r + \theta_{r0,n}$,
$N_{ho}$: Largest index value among nonzero Fourier coefficient components,
J: Number of exposure sets measured for rotation period time T,
$T_i$: Integration time, and
$T_d$: Delay time.

10. An achromatic rotating-element ellipsometer, comprising:
- a light source configured to radiate incident light toward a sample;
- a fixed polarizer configured to be disposed between the light source and the sample on a travel path of the incident light and polarize the incident light radiated from the light source;
- a constant speed rotation polarizer configured to be disposed between the fixed polarizer and the sample on the travel path of the incident light, have the light passing through the fixed polarizer be incident thereon, and rotate at a constant speed for polarizing the incident light;
- a constant speed rotation analyzer configured to have the light polarized by passing through the constant speed rotation polarizer incident thereon and rotate at a constant speed for polarizing the incident light, with a polarization state of the light polarized by passing through the constant speed rotation polarizer being changed by being reflected from or transmitted through the sample;
- a fixed analyzer configured to have the light polarized by passing through the constant speed rotation analyzer incident thereon and polarize the incident light;
- a photodetector configured to have the light polarized by passing through the fixed analyzer incident thereon, detect an exposure of the incident light, and output a value of a radiant flux of the light corresponding to the exposure; and
- an operator configured to calculate a Mueller-matrix component of the sample from a Fourier coefficient for a radiant flux waveform of light calculated from the value of the radiant flux of the light output from the photodetector,
- wherein the constant speed rotation polarizer rotates at a predetermined multiple of a reference angular velocity, the constant speed rotation analyzer rotates at another predetermined multiple of the reference angular velocity, and the photodetector at least outputs the value of the radiant flux of the light for a rotation period of the reference angular velocity, wherein an Equation for the exposure is $S_j = \int_{(j-1)T/J+T_d}^{(j-1)T/J+T_d+T_i} I(t)dt$, $(j=1, \ldots, J)$, and corrected Fourier coefficient values of the radiant flux waveform of the light are $$I_0 = \gamma \sum_{j=1}^{u} \sum_{k=1}^{v} i_{0,jk} M_{jk} = \gamma i_0 \cdot V^{(SP)},$$

$$A_n = \gamma \sum_{j=1}^{u} \sum_{k=1}^{v} a_{n,jk} M_{jk} = \gamma a_n \cdot V^{(SP)}, \text{ and}$$

$$B_n = \gamma \sum_{j=1}^{u} \sum_{k=1}^{v} b_{n,jk} M_{jk} = \gamma b_n \cdot V^{(SP)}, \text{ wherein}$$

$$I(\theta_r) = I_0 + \sum_{n=1}^{N_{ho}} [A_n\cos(n\theta_r) + B_n\sin(n\theta_r)]:$$

Radiant flux waveform of light, $I_0$: Direct current component of corrected Fourier coefficient of radiant flux waveform of light, $A_n, B_n$: Alternating current component of corrected Fourier coefficient of radiant flux waveform of light, $\theta_r$: Azimuth variation due to reference angular velocity measured for real origin, $-\theta_{r0,n}$: Value of $\theta_r$ when t=0, $\omega t = \theta_r + \theta_{r0,n}$, $N_{ho}$: Largest index value among nonzero Fourier coefficient components, J: Number of exposure sets measured for rotation period time T, $T_i$: Integration time, $T_d$: Delay time, $V^{(SP)} = (M_{11}, \ldots, M_{1v}, \ldots, M_{u1}, \ldots, M_{uv})^T$: Solution by which Mueller-matrix component for the sample is represented by vector, $i_0 = (\partial I_0/\partial M_{11}, \ldots, \partial I_0/\partial M_{1v}, \ldots, \partial I_0/\partial M_{u1}, \ldots, \partial I_0/\partial M_{uv})/\gamma$, $a_n = (\partial A_n/\partial M_{11}, \ldots, \partial A_n/\partial M_{1v}, \ldots, \partial A_n/\partial M_{u1}, \ldots, \partial A_n/\partial M_{uv})/\gamma$, $b_n = (\partial B_n/\partial M_{11}, \ldots, \partial B_n/\partial M_{1v}, \ldots, \partial B_n/\partial M_{u1}, \ldots, \partial B_n/\partial M_{uv})/\gamma$, $\gamma = \kappa(1 + d_{12}\cos 2A + d_{13}\sin 2A)(1 + l_1\cos 2P + l_2\sin 2P)$: Common factor associated with a transmittance state of an optical element, P, A: Azimuth positions at real origin coordinate system of property axes of the fixed polarizer and the fixed analyzer, $M^{(SP)} = (M_{jk})_{4\times 4}$: Mueller-matrix of sample, $\kappa = \mu_{QE} A_{PDE} T_{PSA} T_{PSG} D_{11} L_0$, $d_{12(13)} = D_{12(13)}/D_{11}$, $l_{1(2)} = L_{1(2)}/L_0$, $\mu_{QE}$: Quantum efficiency of photodetector, $A_{PDE}$: Effective measurement area of photodetector, $T_{PSG}, T_{PSA}$: Effective transmission coefficient of polarization state generator and polarization state analyzer, u, v: Predetermined integer differently given depending on a type of optical element rotation type spectroscopic ellipsometer used, $S^{(LS)} = (L_0, L_1, L_2, L_3)T$: Stokes vector of light wave incident to pass through polarization state generator, $M^{(DOS)} = (D_{jk})_{4\times 4}$: Mueller-matrix of detector optic system (DOS) disposed between polarization state analyzer and photodetector, PSG: Polarization state generator including fixed polarizer and constant speed rotation polarizer, and PSA: Polarization state analyzer including constant speed rotation analyzer and fixed analyzer.

* * * * *